United States Patent
Garrait et al.

(10) Patent No.: US 10,227,277 B2
(45) Date of Patent: Mar. 12, 2019

(54) PROCESS FOR THE SEPARATION OF 2-CHLORO-1,1-DIFLUOROETHANE AND TRANS-DICHLOROETHYLENE

(71) Applicant: ARKEMA FRANCE, Colombed (FR)

(72) Inventors: Dominique Garrait, Charly (FR); David Andre, Brignais (FR); Abdelatif Baba-Ahmed, Saint-Fons (FR); Charlotte Herdt, Poissy (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 15/551,789

(22) PCT Filed: Feb. 15, 2016

(86) PCT No.: PCT/EP2016/053192
§ 371 (c)(1),
(2) Date: Aug. 17, 2017

(87) PCT Pub. No.: WO2016/131782
PCT Pub. Date: Aug. 25, 2016

(65) Prior Publication Data
US 2018/0029962 A1    Feb. 1, 2018

(30) Foreign Application Priority Data
Feb. 17, 2015 (FR) ..................... 15 51312

(51) Int. Cl.
C07C 17/383    (2006.01)
C07C 17/386    (2006.01)
C07C 19/12     (2006.01)
C07C 21/073    (2006.01)

(52) U.S. Cl.
CPC .......... *C07C 17/383* (2013.01); *C07C 17/386* (2013.01)

(58) Field of Classification Search
CPC ..... C07C 17/386; C07C 17/383; C07C 19/12; C07C 21/073
See application file for complete search history.

(56) References Cited

U.S. PATENT DOCUMENTS 5,874,657 A * 2/1999 Miller .................. C07C 17/386
570/178

FOREIGN PATENT DOCUMENTS

WO    WO 2013/053800 A2    4/2013
WO    WO 2015/082812 A1    6/2015

OTHER PUBLICATIONS

International Search Report (PCT/ISA/210) dated Mar. 24, 2016, by the European Patent Office as the International Searching Authority for International Application No. PCT/EP2016/053192.
Written Opinion (PCT/ISA/237) dated Mar. 24, 2016, by the European Patent Office as the International Searching Authority for International Application No. PCT/EP2016/053192.
Lee F-M, "Extractive Distillation: Close-Boiling-Point", Chemical Engineering, Access Intelligence Association, Rockville, MA, US, vol. 105, No. 12, Nov. 1, 1998, pp. 112-121.
Berg L, "Selecting the Agent for Distillation", Chemical Engineering Process, vol. 65, No. 9, Sep. 1, 1969, pp. 52-57.

* cited by examiner

*Primary Examiner* — Jafar F Parsa
(74) *Attorney, Agent, or Firm* — Buchanan Ingersoll & Rooney P.C.

(57) ABSTRACT

The invention relates to the separation of a mixture comprising 2-chloro-1,1-difluoroethane (R142) and trans-dichloroethylene (TDCE) by extractive distillation and more particularly to a separation process wherein the TDCE is removed selectively by extractive distillation, thus leading to purified 2-chloro-1,1-difluoroethane.

19 Claims, 1 Drawing Sheet

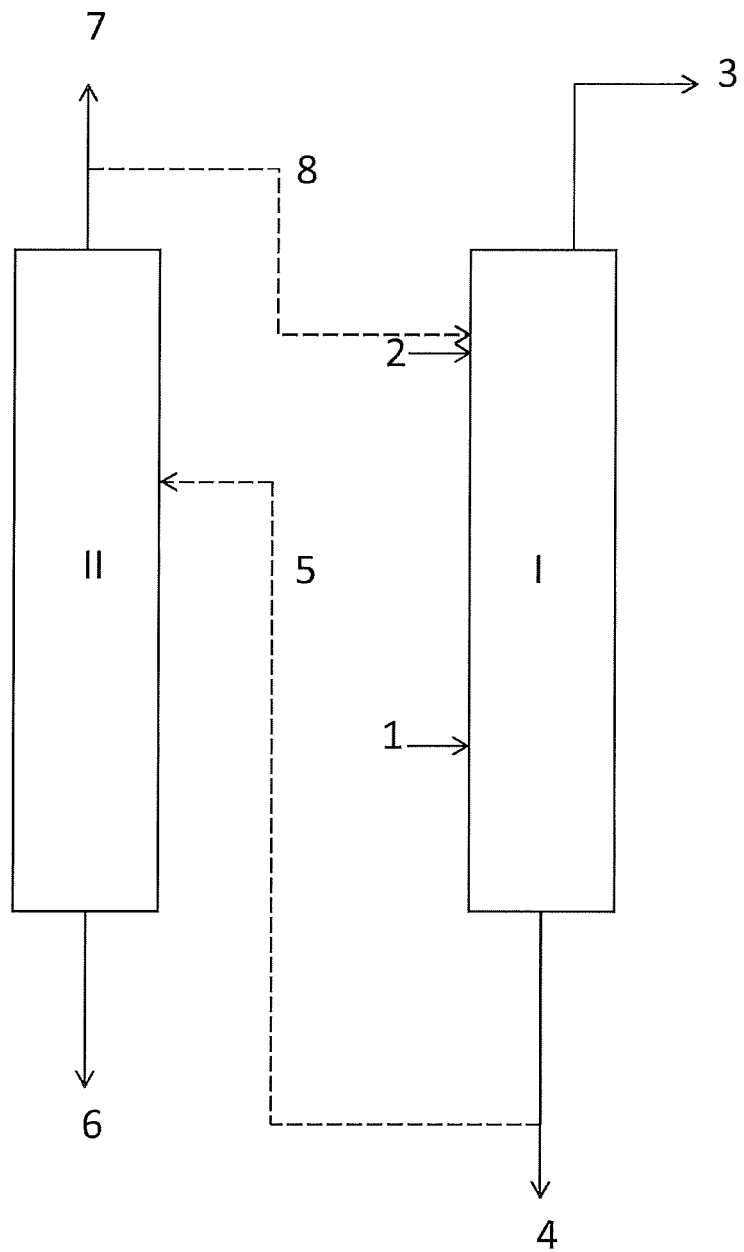

PROCESS FOR THE SEPARATION OF 2-CHLORO-1,1-DIFLUOROETHANE AND TRANS-DICHLOROETHYLENE

FIELD OF THE INVENTION

The invention relates to the separation of a mixture comprising 2-chloro-1,1-difluoroethane (R142) and trans-dichloroethylene (TDCE) by extractive distillation and its subject-matter is more particularly a separation process wherein TDCE is selectively removed by extractive distillation, thus leading to purified 2-chloro-1,1-difluoroethane.

TECHNICAL BACKGROUND

2-Chloro-1,1-difluoroethane (HCFC-142 or R142) is used as blowing agent in the manufacture of foams, or as raw material in the manufacture of pharmaceutical or agrochemical compounds.

2-Chloro-1,1-difluoroethane can be obtained by fluorination of 1,1,2-trichloroethane (T112). This fluorination reaction generates a by-product, trans-dichloroethylene (TDCE), in not insignificant quantities. In order to guarantee a satisfactory purity of the final product, the TDCE should be removed as completely as possible from the mixture obtained at the end of the reaction.

WO 2013/053800 describes a catalytic fluorination process of 1,1,2-trichloroethane and/or of 1,2-dichloro-ethene in the presence of HF in order to obtain 1-chloro-2,2-difluoroethane. This document describes a step wherein 1,2-dichloro-ethene and 1,1,2-trichloroethane are separated from 1-chloro-2,2-difluoroethane by distillation. This document does not describe the process according to the invention comprising a step of extractive distillation.

The existence of an azeotrope or quasi-azeotrope R142/TDCE makes the complete separation of the R142 and TDCE by simple distillation very difficult.

SUMMARY OF THE INVENTION

The invention firstly relates to a process for the separation of a mixture comprising 2-chloro-1,1-difluoroethane and trans-dichloroethylene by extractive distillation.

The process according to the invention is simple to implement, in particular on an industrial scale.

The process according to the invention makes it possible to recover 2-chloro-1,1-difluoroethane with a higher purity. Purities greater than or equal to 95%, or even greater than or equal to 98%, even better, greater than or equal to 99% can thus be obtained.

According to an embodiment, an extraction agent is utilized, which selectively absorbs TDCE.

According to another embodiment, an extraction agent is utilized, which selectively absorbs R142.

According to yet another embodiment, the process according to the invention uses T112, a starting reagent in the manufacture of R142, as extraction agent, which is optimal from an industrial point of view. Indeed, by using T112, it is not necessary to subsequently separate the T112 from the TDCE as the T112-impurities mixture can be reused as it is in the R142 manufacturing process.

The process according to the invention has a satisfactory selectivity and/or capacity for the recovery of the desired species.

BRIEF DESCRIPTION OF THE FIGURE

FIG. 1 is a diagram representing an embodiment of the invention.

DESCRIPTION OF EMBODIMENTS OF THE INVENTION

The invention is now described in more detail and non-limitatively in the description which follows.

The present invention proposes a process for the separation of a mixture comprising R142 ($CHF_2$—$CH_2Cl$) and TDCE ($CHCl$=$CHCl$) by extractive distillation.

The extractive distillation is carried out using an extraction agent, also called extracting agent or solvent, which has a stronger affinity to one of the two compounds of the mixture.

The principle of extractive distillation is well known to a person skilled in the art.

In an extractive distillation process, the separation of the constituents of a binary mixture is carried out using a so-called extraction column (column I) comprising successively, from the boiler at the top, three sections, one of depletion, the second of absorption and the third of recovery.

The binary mixture to be fractionated is injected at the top of the depletion section (flow 1) while the one-third acting as selective solvent or extraction agent is introduced at the top of the absorption section (flow 2) in order to circulate in the liquid state from its point of introduction as far as the boiler.

The third so-called recovery section serves to separate by distillation the least absorbed constituent (flow 3), from the traces of solvent entrained under the effect of its non-zero vapour pressure.

A column for regeneration of the solvent (column II) makes it possible to separate the solvent/absorbed constituent mixture (flow 5) according to the difference in their boiling points. The recovered solvent (flow 7) can be reused for extraction in the column I (flow 8).

The diameter and the number of stages of the extractive distillation column, the reflux ratio and the optimum temperatures and pressures can be easily calculated by a person skilled in the art from the data specific to the individual constituents and to mixtures thereof (relative volatilities, vapour pressures and physical constants).

According to an embodiment of the invention, the distillation is carried out under a pressure ranging from 0.005 bar to 10 bar, preferably from 0.3 bar to 4 bar.

The distillation can be carried out at a temperature ranging from −50° C. to 250° C., preferably from −20° C. to 185° C., and more preferably from 5° C. to 145° C.

According to an embodiment of the invention, the extractive distillation is carried out using a molar ratio of extracting agent/product to be removed ranging from 0.01 to 20, preferably from 0.1 to 10, and more preferably from 0.5 to 10.

The mixture to be separated comprises at least 2-chloro-1,1-difluoroethane and TDCE. As indicated previously, the mixture comprising R142 and TDCE can be obtained at the end of a fluorination reaction of T112 ($CHCl_2$—$CH_2Cl$).

According to an embodiment, the R142/TDCE molar ratio in the mixture before extractive distillation ranges from 2 to 100, preferably from 2 to 50, more preferably from 3 to 30.

According to an embodiment, the R142/TDCE molar ratio after extractive distillation ranges from 9 to 99,999, preferably from 20 to 9,999, more preferably from 40 from 9,999.

Depending on the choice of extraction agent, said extraction agent can selectively absorb either the R142, or the TDCE.

According to a first embodiment, the extraction agent selectively absorbs TDCE.

In this first embodiment, the extraction agent then preferably has a separation factor F at 25° C., as defined below, greater than 1.1, preferably greater than 1.4, more preferably greater than 2.

The separation factor (F) is defined as follows:

$$F = \frac{\gamma(R142)}{\gamma(TDCE)} \times \frac{P(R142)}{P(TDCE)}$$

where $\gamma(R142)$ represents the activity coefficient of the compound R142 in the solvent considered at infinite dilution.

$\gamma(TDCE)$ represents the activity coefficient of the compound TDCE in the solvent considered at infinite dilution.

P(R142) represents the vapour pressure of the compound R142 at the temperature considered.

P(TDCE) represents the vapour pressure of the compound TDCE at the temperature considered.

The P(R142)/P(TDCE) ratio corresponds to the relative volatility of R142 with respect to TDCE.

The activity coefficient values of the compounds i (i is R142 or TDCE), $\gamma_i$, are calculated according to the relationship:

$$\ln \gamma_j = (\mu_j^i - \mu_j^p)/RT,$$

where $\mu_j^i$ corresponds to the chemical potential of the compound i at infinite dilution in the solvent considered, and $\mu_j^p$ corresponds to the chemical potential of the pure compound i, and R is the perfect gas constant, and T is the temperature.

The activity coefficient and the vapour pressure are well-known data, accessible to a person skilled in the art.

In a second embodiment, the extraction agent selectively absorbs the R142. In this case, the extraction agent then has a separation factor, as defined above, less than 1, preferably less than 0.9, more preferably less than 0.7, and even more preferentially less than 0.5.

According to this second embodiment and with reference to FIG. 1, the flow 1 comprising the R142/TDCE mixture to be separated is introduced into distillation column I and the flow 2 comprising the extraction agent is introduced into column I via a different inlet. According to this embodiment, the flow 3 comprises mainly TDCE and the flow 4 comprises mainly R142 and extraction agent. In order to recover the purified R142, the flow 4 is sent to a distillation column II wherein a flow 5 comprising the R142 and the extraction agent is separated in order to obtain a flow 6 comprising mainly R142 and a flow 7 comprising mainly extraction agent. The flow 7 can then be reintroduced into the column I for the extractive distillation.

According to an embodiment, the process according to the invention is implemented using an extraction agent which is chosen from:

the compounds having a boiling point greater than 35° C., preferably greater than or equal to 50° C., more preferably greater than or equal to 60° C., and/or the compounds having a dipole moment less than or equal to 5 Debye, preferably less than or equal to 4.5 Debye, more preferably less than or equal to 4 Debye, preferably less than or equal to 3 Debye, more preferably less than or equal to 2 Debye.

The dipole moment is a data well-known to a person skilled in the art. The dipole moment illustrates the electrical heterogeneity of molecules, and reflects the fact that the barycentre of the positive charges of a molecule do not coincide with the barycentre of the negative charges of the molecule. The dipole moment is generally expressed in Debye units (1 Debye=3.33 $10^{-30}$ C·m), and there are tabulated databases making it possible to access the dipole moments of numerous molecules. In the absence of a known accessible value, it can also be measured using standardized protocols that are well-known to a person skilled in the art, in particular those based on the correlation between the dielectric constants of the media and the dipole moments. For information purposes, the details of such protocols are given below.

According to an embodiment, the extraction agent can be chosen from the linear, branched or non-branched, cyclic or aromatic, saturated or unsaturated, optionally substituted hydrocarbons.

Preferably, the hydrocarbon is substituted and in this case the substituent(s) can be chosen from a nitrogen atom, an oxygen atom, a halogen atom, an alcohol function or an amine function, and preferably the hydrocarbon is substituted with at least one halogen atom, preferably with at least one chlorine atom.

Preferably, the hydrocarbons have from 1 to 12 carbon atoms, preferably from 1 to 10 carbon atoms, more preferably from 1 to 8 carbon atoms.

According to an embodiment, the extraction agent is chosen from the linear, branched or non-branched, cyclic or aromatic hydrocarbons comprising from 6 to 8 carbon atoms, such as hexane, cyclohexane, methylcyclohexane, n-heptane, octane, 2-methylpentane or toluene.

According to an embodiment, the extraction agent is chosen from the linear, branched or non-branched, cyclic or aromatic hydrocarbons substituted with at least one oxygen atom. According to this embodiment, the extraction agent can be an alcohol, such as 1-butanol or 1-decanol.

According to an embodiment, the extraction agent is chosen from the linear, branched or non-branched, cyclic or aromatic hydrocarbons substituted with at least one nitrogen atom. According to this embodiment, the extraction agent can be an amine, such as N-ethyl-2-dimethylaminoethylamine.

According to another embodiment, the extraction agent is chosen from the halogenated hydrocarbons comprising from 2 to 4 halogen atoms. Among the halogenated hydrocarbons which can be used, tetrachloromethane, 1,1,2-trichloroethane, 1,1,1-trichloroethane, tetrachloroethene, 1,1,2,2-tetrachloroethane, 1,1,1,2-tetrachloroethane, trichloroethene, tribromomethane or triiodomethane may be mentioned.

According to an embodiment, the extraction agent is 1,1,2-trichloroethane (T112). Preferably, the T112 originates from the manufacturing process for R142. The process according to the invention being able to use T112 as extraction agent has a significant economic benefit since the TT12 selectively extracts the TDCE. With reference to FIG. 1, it is not necessary in this embodiment to separate the T112 comprising TDCE in a second distillation column II, the flow comprising T112 and TDCE being able to be used as it is in the synthesis of R142.

Examples

Different solvents were assessed. The characteristics of these solvents are shown in Table 1.

TABLE 1

Characteristics of the solvents

| | Dipole moment (Debye) | Boiling point (° C.) |
|---|---|---|
| 1,1,2-trichloroethane | 1.55 | 114 |
| CCl$_4$ | 0 | 76.7 |
| 2-methoxyethanol | 2.36 | 124 |
| 1,1,1-trichloroethane | 1.781 | 74 |
| Cyclohexane | 0 | 80 |
| Toluene | 0.36 | 111 |
| Methylcyclohexane | 0 | 100.85 |
| n-heptane | 0 | 98 |
| Hexane | 0 | 68 |
| Octane | 0 | 125 |
| Tetrachloroethene | 0 | 121 |
| 1,1,2,2-tetrachloroethane | 1.289 | 130.5 |
| 1,1,1,2-tetrachloroethane | 1.289 | 146 |
| Trichloroethene | 0.77 | 87 |
| n-methyl-2-pyrrolidone | 4.077 | 202 |
| 2-methylpentane | 0 | 60.3 |
| tribromomethane | 0.99 | 150 |
| N-ethyl-2-dimethylaminoethylamine | — | 134.5 |
| triiodomethane | 0.9 | 218 |
| 1-decanol | 1.619 | 233 |
| 1-butanol | 1.661 | 117.7 |

The selectivity, capacity and separation factor for these different solvents were determined and are shown in Table 2 below.

The selectivity corresponds to the ratio of the activity coefficients at infinite dilution of the R142 (γ142) and TDCE (γTDCE) in the solvent for the same partial pressure and at the same temperature.

The capacity represents the inverse of the activity coefficient at infinite dilution of the compound i in the solvent j considered.

The separation factor F represents the corrected selectivity of the relative volatility, as already defined previously.

$$F = \frac{\gamma(R142)}{\gamma(TDCE)} \times \frac{P(R142)}{P(TDCE)}$$

TABLE 2 parameters of the separation

| | γ (TDCE) | γ (R142) | selectivity | capacity | Separation factor |
|---|---|---|---|---|---|
| 1,1,2-trichloroethane | 1.08 | 1.49 | 1.37 | 0.92 | 2.17 |
| CCl$_4$ | 1.15 | 4.04 | 3.52 | 0.87 | 5.55 |
| 2-methoxyethanol | 0.87 | 0.78 | 0.91 | 1.15 | 1.43 |
| 1,1,1-trichloroethane | 1.01 | 1.89 | 1.88 | 0.99 | 2.97 |
| Cyclohexane | 1.33 | 4.52 | 3.40 | 0.75 | 5.36 |
| Toluene | 0.91 | 1.47 | 1.62 | 1.10 | 2.55 |
| Methylcyclohexane | 1.30 | 4.37 | 3.36 | 0.77 | 5.31 |
| n-heptane | 1.32 | 4.16 | 3.15 | 0.76 | 4.97 |
| Hexane | 1.37 | 4.23 | 3.08 | 0.73 | 4.87 |
| Octane | 1.28 | 4.10 | 3.21 | 0.78 | 5.07 |
| Tetrachloroethene | 1.15 | 4.28 | 3.72 | 0.87 | 5.87 |
| 1,1,2,2-tetrachloroethane | 1.02 | 1.88 | 1.84 | 0.98 | 2.91 |
| 1,1,1,2-tetrachloroethane | 0.98 | 1.97 | 2.02 | 1.02 | 3.18 |
| Trichloroethene | 1.04 | 2.66 | 2.55 | 0.96 | 4.03 |
| n-methyl-2-pyrrolidone | 0.20 | 0.16 | 0.77 | 4.96 | 1.22 |
| 2-methylpentane | 1.38 | 4.19 | 3.04 | 0.73 | 4.81 |
| tribromomethane | 4.06 | 1.01 | 4.00 | 0.98 | 6.30 |
| N-ethyl-2-dimethylaminoethylamine | 0.16 | 0.61 | 3.81 | 6.38 | 6.10 |
| triiodomethane | 1.27 | 6.34 | 4.99 | 0.78 | 7.80 |
| 1-decanol | 0.93 | 2.08 | 2.20 | 3.53 | 5.70 |
| 1-butanol | 1.28 | 1.87 | 1.50 | 0.78 | 2.31 |

Table 2 shows that the 1,1,2-trichloroethane (T112) has a separation factor greater than 2. When the R142/TDCE mixture originates from a fluorination reaction of T112, a process of separation by extractive distillation using T112 as extraction agent is very optimal from an industrial point of view.

Table 2 also shows that tetrachloroethene has an excellent separation factor.

Protocol for Determination of the Dipole Moments:

Unlike the dielectric constant which is an overall property of the medium, the dipole moment is a property of the molecule. However, these two characteristics are linked. The experimental determination of the dielectric constant, also called relative permittivity, allows relatively simple experimental determination of the dipole moment. The dipole moment of a substance can be determined from the constants of the pure product in the liquid state, or of solutions (apolar solvents) comprising the product to be characterized. It can also be calculated by the additivity of the bond moments.

Different, more or less complex experimental techniques can be used. Among different approaches, use is in general made of the dependence between the dielectric constant of a solution and the dipole moment of the molecules. The dielectric constant is measured relatively easily by measuring the electrical capacity of a cell containing the solution to be studied (indeed, the capacity is proportional to the dielectric constant and the proportionality constant depends only on the geometry of the cell used for the measurement).

The test thus consists of firstly measuring the capacity of the measurement cell when empty, $C_0$, then the measurement of the capacity of the full cell, C, leads to determination of the relative permittivity $\epsilon_r = C/C_0$.

Devices such as IRLAB can be suitable for this type of measurement, but any other multimeter that can accurately measure electrical capacities can be suitable.

In order to determine the dipole moment, it is also necessary to determine the refractive index of the product. For this, a refractometer must be used.

1. Determination of the Dipole Moment from the Constants of the Pure Product in the Liquid State Several theories have been developed in an attempt to link the dipole moment and the dielectric constant of a pure product in the liquid state. Among these, we have adopted ONSAGER's theory which leads to the following equation:

$$\mu_0^2 = \frac{9\epsilon_0 kT}{N} \cdot \frac{M}{\rho} \cdot \frac{(2\epsilon + \epsilon_\infty)(\epsilon + 2)}{3\epsilon(\epsilon_\infty + 2)} \cdot \left[ \frac{\epsilon - 1}{\epsilon + 2} - \frac{\epsilon_\infty - 1}{\epsilon_\infty + 2} \right]$$

In this formula, the different constants have the following meanings:

$\mu_0$: permanent dipole moment of the molecule.
$\epsilon_0$: Vacuum permittivity, equal to 8.85, $10^{-12}$ J$^{-1}$·C2·m$^{-1}$ k: Boltzmann's constant, equal to $1.38 \cdot 10^{-23}$ J·K$^{-1}$·mole$^{-1}$
T: Absolute temperature in Kelvin.
N: Avogadro's number, equal to $6.0238 \cdot 10^{23}$ mole$^{-1}$
M: Molecular mass of the substance, in kilograms.
ρ: Density of the substance at temperature T
∈: Dielectric constant of the substance at temperature T
∈$_\alpha$: "optical dielectric constant"

The "optical dielectric constant" ∈$_\alpha$ can be obtained as the square of the refractive index of the substance for the sodium D-line.

This theory assumes that the polar molecules are spherical. It takes into account the strong molecular interactions originating from the permanent dipoles and, in order to take these into account, it introduces the "reaction field of a dipole". However, this theory ceases to be valid when interactions orientated towards a short radius of action occur, as is the case for substances having intermolecular hydrogen bonds.

2. Determination of the Dipole Moment from Solutions

In the case of the dilute solution of a polar compound in a non-polar solvent, the molecular interactions can be disregarded This makes it possible to apply DEBYE's equation to the solutions.

The polarization of a solution can be considered in a first approximation as a linear function of its concentration.

These data were exploited by GUGGENHEIM and SMITH in order to calculate the dipole moment of the solute as a function of the variations in the dielectric constant and refractive index of the solution with the concentration.

The following formula is used:

$$\mu_0^2 = \frac{27\varepsilon_0 kT}{N} \cdot \frac{1}{\rho_1(\varepsilon_1+2)^2} \cdot (a_0 - a_n) \cdot M$$

In this formula $\mu_0$, ∈$_0$, k, T, N and M have the same meaning as in ONSAGER's formula (see above).

ρ$_1$: density of the solvent
μ$_1$: dielectric constant of the solvent
$a_\in$: Slope of the straight line ∈$_{12}$−∈$_1$=f(x)
$a_n$: Slope of the straight line $n_{12}^2 - n_1^2$=f(x)
$n_1$: Refractive index of the solvent
∈$_{12}$: Dielectric constant of the solutions
$n_{12}$: Refractive index of the solutions
x: Ratio of the weight of solute to the weight of solution

The invention claimed is:

1. A process for the separation of a mixture comprising 2-chloro-1,1-difluoroethane and trans-dichloroethylene by extractive distillation.

2. The separation process according to claim 1, wherein the 2-chloro-1,1-difluoroethane/trans-dichloroethylene molar ratio before extractive distillation ranges from 2 to 100.

3. The separation process according to claim 1, wherein the 2-chloro-1,1-difluoroethane/trans-dichloroethylene molar ratio after extractive distillation ranges from 9 to 99.999.

4. The separation process according to claim 1, wherein the extractive distillation is carried out under a pressure ranging from 0.05 bar to 10 bar.

5. The separation process according to claim 1, wherein the extractive distillation is carried out at a temperature ranging from −50° C. to 250° C.

6. The separation process according to claim 1, wherein the extractive distillation is carried out using an extracting agent/product to be removed molar ratio ranging from 0.01 to 20.

7. The separation process according to claim 1, wherein the mixture comprising 2-chloro-1,1-difluoroethane and trans-dichloroethylene originates from a fluorination reaction of 1,1,2-trichloroethane.

8. The separation process according to claim 1, wherein an extraction agent is utilized, consisting of compounds having a boiling point greater than 35° C.

9. The separation process according to claim 1, wherein an extraction agent is utilized, having a dipole moment less than or equal to 5 Debye.

10. The separation process according to claim 8, wherein the separation factor of the 2-chloro-1,1-difluoroethane and trans-dichloroethylene in the extraction agent is greater than 1.1.

11. The separation process according to claim 8, wherein the separation factor of the 2-chloro-1,1-difluoroethane and trans-dichloroethylene in the extraction agent is less than 1.

12. The separation process according to claim 8, wherein the extraction agent is a hydrocarbon selected from the linear, branched or non-branched, cyclic or aromatic, saturated or unsaturated hydrocarbons, optionally substituted.

13. The separation process according to claim 12, wherein the optionally substituted hydrocarbons have from 1 to 12 carbon atoms.

14. The separation process according to claim 12, wherein the hydrocarbons are substituted with at least one substituent chosen from an oxygen atom, a nitrogen atom, a halogen atom, an alcohol group, an amine group.

15. The separation process according to claim 8, wherein the extraction agent is chosen from the linear, branched, cyclic or aromatic hydrocarbons comprising from 6 to 8 carbon atoms.

16. The separation process according to claim 15, wherein the extraction agent is chosen from hexane, cyclohexane, methylcyclohexane, n-heptane, octane, 2-methylpentane or toluene.

17. The separation process according to claim 8, wherein the extraction agent is chosen from the halogenated hydrocarbons comprising from 2 to 4 halogen atoms.

18. The separation process according to claim 17, wherein the halogenated hydrocarbons are chosen from tetrachloromethane, 1,1,2-trichloroethane, 1,1,1-trichloroethane, tetrachloroethene, 1,1,2,2-tetrachloroethane, 1,1,1,2-tetrachloroethane, trichloroethene, tribromomethane or triiodomethane, preferably 1,1,2-trichloroethane and tetrachloroethene.

19. The separation process according to claim 7, wherein the extraction agent is 1,1,2-trichloroethane originating from said fluorination reaction.

* * * * *